(12) United States Patent
Reddy et al.

(10) Patent No.: US 6,541,475 B2
(45) Date of Patent: Apr. 1, 2003

(54) α, β-UNSATURATED SULFONES FOR TREATING PROLIFERATIVE DISORDERS

(75) Inventors: E. Premkumar Reddy, Villanova, PA (US); M. V. Ramana Reddy, Upper Darby, PA (US)

(73) Assignee: Temple University - Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/833,834

(22) Filed: Apr. 12, 2001

(65) Prior Publication Data

US 2002/0028818 A1 Mar. 7, 2002

Related U.S. Application Data

(60) Provisional application No. 60/197,368, filed on Apr. 14, 2000.

(51) Int. Cl.[7] ...................... A61K 31/495; A61K 31/38; C07D 295/00; C07D 333/00; C07D 307/06

(52) U.S. Cl. .................. 514/252.12; 514/277; 514/365; 514/428; 514/438; 514/446; 514/447; 514/461; 544/398; 546/339; 548/208; 548/562; 549/78; 549/497

(58) Field of Search ............... 549/78, 497; 514/438, 514/277, 252.12, 446, 461, 365, 428, 447; 544/398; 546/339, 398; 548/208, 562

(56) References Cited

U.S. PATENT DOCUMENTS

| | | | |
|---|---|---|---|
| 2,532,612 A | 12/1950 | Doumani | 260/609 |
| 3,185,743 A | 5/1965 | Combe et al. | 260/682 |
| 3,418,101 A | 12/1968 | Buchholtz et al. | 71/72 |
| 3,514,386 A | 5/1970 | Oswald et al. | 204/162 |
| 3,917,714 A | 11/1975 | Richmond | 260/607 A |
| 4,161,407 A | 7/1979 | Campbell | 96/114 |
| 4,386,221 A | 5/1983 | Hyatt et al. | 568/28 |
| 4,937,388 A | 6/1990 | Bushell et al. | 568/56 |
| 5,659,087 A | 8/1997 | Aikins et al. | 568/27 |

FOREIGN PATENT DOCUMENTS

| | | | |
|---|---|---|---|
| WO | WO99/18068 | | 4/1999 |
| WO | 9918068 | * | 4/1999 |

OTHER PUBLICATIONS

Reddy et al. Preparation of styryl benzylsulfones and 1,2–bis–(styrylsufonylmethyl)–4,5–dimethylbenzenes. Org. Prep. Proc. Int. 20, 205–212, 1988.*

Reddy et al. Synthesis and cyclopropanation of (E)—and (Z)–styryl benzyl sulfones, Sulfur Lett. 13, 83–90, 1991.*

Reddy et al. Synthesis of α, β–unsaturated sulfones. Acta Chim. Hung. 115, 269–271, 1984.*

Reddy et al. Synthesis of some novel α, β–ethylenic sulfones. Phosphorus, Sulfur, and Silicon 60, 209–214, 1991.*

Reddy et al. Synthesis and spectral studies of some (E)–α–[(aryl)sulfonyl]chalones. Acta. Chim. Hung. 120, 275–280, 1985.*

Reddy et al. A novel synthesis of (E)–substituted styryl (Z)–styryl sulfones. Synthesis pp. 322–323, 1984.*

Reddy et al. A facile method for the synthesis of 2–(arylsulfonyl)–1–phenyl–3–aryl–2–propen–1–ones. Sulfur Lett. 7, 43–48, 1987.*

Reddy et al. A new route for the synthesis of styrylbenzyl-sulfones, precursors of 1–benzylsulfonyl–2–arylcyclopropanes. Phosporus, Sulfur, and Silicon 53, 285–290, 1990.

Makosza et al. Some reactions of the chloromethyl trans–β–styryl sulfone carbanion. Liebigs Ann./Reueil. pp. 2337–2340, 1997.

Reddy et al. Phase transfer catalysis—A facile method for cycloprepanation of some isomeric styryl benzyl sulfones and bis(styryl)–sulfones. Models Chem. 131, 83–92, 1994.

Reddy et al. Synthesis of 1,1–disubstituted 2,6–diaryl–4–thian–4,4–dioxides, part–II. Indian J. Heterocycl. Chem. 5, 11–14, 1995. Abstract.

Reddy et al., E, Z and E, E–bis(styryl)sulfones as precursors for thiane oxides. Indian J. Heterocycl. Chem. 4, 259–264, 1995. Abstract.

Thompson et al. Sulfone metabolits of sulindac inhibits mammary carcinogenesis. Cancer Res. 57, 267–271, 1997. Abstract.

(List continued on next page.)

*Primary Examiner*—Mukund J. Shah
*Assistant Examiner*—Sudhaker B. Patel
(74) *Attorney, Agent, or Firm*—Drinker Biddle & Reath LLP

(57) ABSTRACT

α, β-Unsaturated sulfones of the following formulae are provided, which are useful as antiproliferative agents, including, for example, anticancer agents:

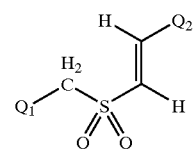

I

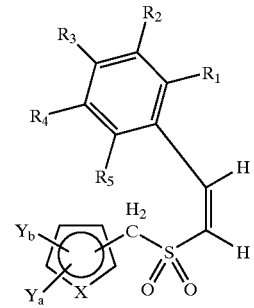

V

41 Claims, No Drawings

OTHER PUBLICATIONS

Benati et al. Free–radical addition of alkanethiols to alkynes. Rearrangements of the intermediate β–thiovinyl radicals. J. Org. Chem. 59, 2818–2823, 1994.

Reddy et al. Synthesis and reactivity of some new mono–and bis (2–pyrazolyl) sulfones. Sulfur Lett. 16, 227–235, 1993.

Reddy et al. Stereospecific synthesis of some new Z–and E–cuclopropyl benzyl sulfones and E, Z–and E,E–bis (cyclopropyl) sulfones by PTC method. Phosphorus, Sulfur silicon Relat. Elem. 90, 1–10, 1994. Abstract.

Reddy et al. Tetrahydro–1,4–thiazine–1,1–dioxides. Part IV. Synthesis and conformational analysis of some 2,3,5–trisubstituted tetrahydro–1,4–thiazine–1,1–dioxides. Indian J. Chem, Sect. B. Org. Chem. Incl. Med. Chem. 34B, 816–822. Abstract.

Findlay et al. Chemical protectors against sunburn. Optical evaluation, with special reference to p–aminobenzoic acid. Brit. J. Dermattol. Suppl. 7, 44–49, 1971.

Naidu et al. Synthesis of some new bis (styryl) sulfones. Proc. Indian Acad. Sci. Chem. Sci. 95, 391–395, 1985. Abstract.

Konopa et al. Preparation of phenyl sulfones and antitumor agents containing them. Jpn. Kokai Tokkyo Koho JP 09 03,037, Jan. 7, 1997. Abstract.

Cosenza et al. U.S. Patent application Ser. No. 09/689,281, filed Oct. 11, 2000.

D. Bhaskar Reddy, N.S. Reddy, S. Reddy, M.V.R. Reddy and S. Balasubramanyam, *Org. Prep. Proc. Int.*, 20(3):205–212 (1988).

D. Bhaskar Reddy, P. V. Ramana Reddy, V. Padmavathi, and M.V.R. Reddy, *Sulfur Lett.*, 13(2):83–90 (1991) II 102.

M.V.R. Reddy and S. Reddy, *Acta Chim. Acad. Sci. Hung.*, 115(3):269–271 (1984).

M.V.R. Reddy, V. Vijayalakshmi, D. Bhaskar Reddy and P.V. Ramana Reddy, *Phosphorus, Sulfur Silicon Relat. Elem.*, 60:209–214 (1991).

M.V. Reddy and S. Reddy, *Acta Chim. Acad. Sci. Hung.*, 120(4):275–280 (1985).

M.V.R. Reddy and S. Reddy, *Synthesis* No. 4, 322–323 (1984).

M.V.R. Reddy, S. Reddy and D.B. Reddy, *Sulfur Lett.*, 7(2):43–48 (1987).

Reddy et al., "A New Route for the Synthesis of Styrylbenzylsulfones, Precursors of 1–Benzylsulfonyl–2–Arylcyclopropanes", *Phosphorus, Sulfur, and Silicon*, 53:285–290 (1990). III 102.

Mieczyslaw Makosza and Irina Krylova, "Some Reactions of the Chloromethyl trans–beta–Styryl Sulfone Carbanion", *Liebigs Ann./Recueil*, pp. 2337–2340 (1997). I 102.

Reddy et al., "Phase Transfer Catalysis—A Facile Method for Cyclopropanation of Some Isomeric Styrl Benzyl Sulfones and bis(Styryl)Sulfones", *Acta Chim. Hung.*, 131(1):83–92 (1994).

CA:124:175763, abs of Reddy et al., *Indian J. Heterocycli. Chem.*, (May 1995), 5(1), 11–14.

CA:124:146025, abs of Reddy et al., *Indian J. Heterocycl. Chem.* (1995), 4(4), 259–264.

CA:126:166162, Thompson et al. abs of *Cancer Res.*, (Feb. 1997) 57(2), 267–271.

Benati, et al., *J. Org. Chem.*, 59:2818–2823 (1994).

CA:120:323356 abs of Reddy et al., *Sulf. Lett.* (1993), 16(5–6), 227–35.

CA:122:132682 abs of Reddy et al., *Phosphorus, Sulfur Silicon Relat. Elem.* (1994), 90(1–4), 1–10.

CA:124:8731 abs of Reddy et al., *Indian J. Chem. Sec. B: Org. Chem. Incl. Med. Chem.* (1995) 34B(9), 816–22.

CA:76:121420 abs of Findlay et al. *Brit. J. Dermatol.*, Suppl. (1971), No. 7, 44–9.

CA:105:133446 abs of Naidu et al., *Proc.—Indian Acad. Sci., Chem. Sci.* (1985), 95(4), 391–5.

CA:126:185889 abs of Japanese Pat. App. 09–03,037 (Jan. 7, 1997).

U.S. Pat. App. Ser. No. 09/689,281 filed Oct. 11, 2000 of Stephen C. Cosenza, M.V. Ramana Reddy and E. Premkumar Reddy.

* cited by examiner

α, β-UNSATURATED SULFONES FOR TREATING PROLIFERATIVE DISORDERS

CROSS-REFERENCE TO RELATED APPLICATIONS

The benefit of the filing dates of provisional application Serial No. 60/197,368, filed Apr. 14, 2000, is claimed pursuant to 35 U.S.C. 1119(e). The entire disclosures of the aforesaid provisional application is incorporated herein by reference.

FIELD OF THE INVENTION

The invention relates to compositions and methods for the treatment of cancer and other proliferative disorders.

BACKGROUND OF THE INVENTION

Extracellular signals received at transmembrane receptors are relayed into the cells by the signal transduction pathways (Pelech et al., *Science* 257:1335 (1992)) which have been implicated in a wide array of physiological processes such as induction of cell proliferation, differentiation or apoptosis (Davis et al., *J. Biol. Chem.* 268:14553 (1993)). The Mitogen Activated Protein Kinase (MAPK) cascade is a major signaling system by which cells transduce extracellular cues into intracellular responses (Nishida et al., *Trends Biochem. Sci.* 18:128 (1993); Blumer et al., *Trends Biochem. Sci.* 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., *Science* 255:212 (1992); Biggs III et al., *Proc. Natl. Acad. Sci. USA* 89:6295 (1992); Garner et al., *Genes Dev.* 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., *Genes Dev.* 7:2135 (1993)). JNKs are members of the class of stress-activated protein kinases (SPKs). JNKs have been shown to be activated by treatment of cells with UV radiation, pro-inflammatory cytokines and environmental stress (Derijard et al., *Cell* 1025 (1994)). The activated JNK binds to the amino terminus of the c-Jun protein and increases the protein's transcriptional activity by phosphorylating it at ser63 and ser73 (Adler et al., *Proc. Natl. Acad. Sci. USA* 89:5341 (1992); Kwok et al., *Nature* 370:223 (1994)).

Analysis of the deduced primary sequence of the JNKs indicates that they are distantly related to ERKs (Davis, *Trends Biochem. Sci.* 19:470 (1994)). Both ERKs and JNKs are phosphorylated on Tyr and Thr in response to external stimuli resulting in their activation (Davis, *Trends Biochem. Sci.* 19:470 (1994)). The phosphorylation (Thr and Tyr) sites, which play a critical role in their activation are conserved between ERKs and JNKs (Davis, *Trends Biochem. Sci.* 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., *Nature* 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., *Annu Rev Biochem* 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., *Eur. J. Biochem.* 135:583–589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What is also needed are new cell antiproliferative agents, and anticancer therapeutics in particular, which are highly selective in the killing of proliferating cells such as tumor cells, but not normal cells.

SUMMARY OF THE INVENTION

It is an object of the invention to provide compounds, compositions and methods for the treatment of cancer and other proliferative diseases. The biologically active compounds are in the form of certain sulfone compounds.

It is an object of the invention to provide compounds which are highly selective in killing tumor cells but not normal cells.

According to one embodiment of the invention, novel compounds are provided according to formula I:

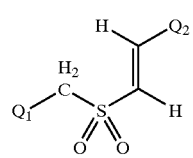

wherein:

$Q_1$ is selected from the group consisting of (a) a phenyl radical according to formula II

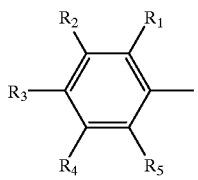

II wherein
  $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
(b) an aromatic radical selected from the group consisting of 1-naphthyl, 2-naphthyl and 9-anthryl; and
(c) an aromatic radical according to formula III

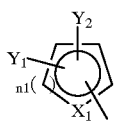

III wherein
  $n_1$ is 1 or 2,
  $Y_1$ and $Y_2$ are independently selected from the group consisting of hydrogen, halogen, and nitro, and
  $X_1$ is selected from the group consisting of oxygen, nitrogen, sulfur and

and
$Q_2$ is selected from the group consisting of (d) a phenyl radical according to formula II

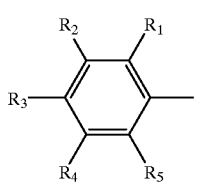

II wherein
  $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
(e) an aromatic radical selected from the group consisting of 1-naphthyl, 2-naphthyl and 9-anthryl;

(f) an aromatic radical according to formula IV

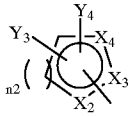

IV wherein
  $n_2$ is 1 or 2,
  $Y_3$ and $Y_4$ are independently selected from the group consisting of hydrogen, halogen, and nitro, and
  $X_2$, $X_3$ and $X_4$ are independently selected from the group consisting of carbon, oxygen, nitrogen, sulfur and

provided that not all of $X_2$, $X_3$ and $X_4$ may be carbon; and
(g) 1-piperazinyl;
  provided that at least one of $Q_1$ or $Q_2$ is other than a phenyl radical according to formula II.;
  or a pharmaceutically acceptable salt thereof.

According to another embodiment of the invention, novel compounds of the Z-configuration are provided according to formula V:

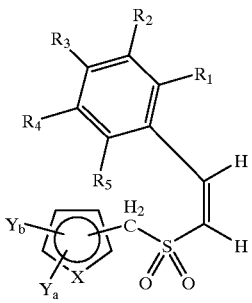

V wherein:
  X is sulfur or oxygen; and $Y_a$ and $Y_b$ are independently selected from the group consisting of hydrogen, halogen, and nitro; and $R_1$ through $R_5$ are defined as above;
  or a pharmaceutically acceptable salt thereof.

According to other embodiments, processes for preparing compounds according to the present invention are provided. In one such embodiment, a compound of formula I is prepared by condensing a compound of the formula Ia

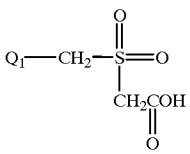

Ia with a compound of the formula

where $Q_1$ and $Q_2$ are defined as above for formula I.

The formula Ia compound may be prepared, for example, by reacting sodium glycollate with a compound of the formula $Q_1CH_2Cl$ to form a thioacetic compound of the formula

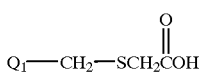

which is then oxidized to form a compound of formula 1a, wherein $Q_1$ is defined as above.

Alternatively, the thioacetic acid compound $Q_1CH_2SCH_2COOH$ is prepared by reacting a compound of the formula $HSCH_2COOR$, where R is C1–C6 alkyl, with the aforementioned $Q_1CH_2$—Cl compound to form a compound of the formula:

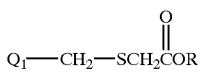

wherein R is C1–C6 alkyl, which is then converted to the corresponding thioacetic acid compound by alkaline or acid hydrolysis.

A process for preparing compounds according to formula V is also provided. A compound of the of the formula

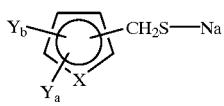

wherein $Y_b$, $Y_a$ and X are defined as above, is reacted with a compound of the formula

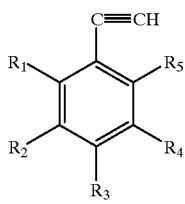

where $R_1$ to $R_5$ are defined above, to form a sulfide compound of formula Va:

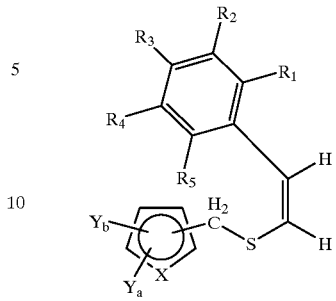

The sulfide compound is then oxidized to form a sulfone compound according to formula V.

The term "alkyl", by itself or as part of another substituent means, unless otherwise stated, a straight or branched chain hydrocarbon radical, including di- and multi-radicals, having the number of carbon atoms designated (i.e. C1–C6 means one to six carbons) and includes straight or branched chain groups. Most preferred is C1–C3 alkyl, particularly ethyl and methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are C1–C3 alkoxy, particularly ethoxy and methoxy.

By "halogen" is meant fluorine, chlorine, bromine or iodine.

By "substituted" means that an atom or group of atoms has replaced hydrogen as the substituent attached to another group.

A pharmaceutical composition is also provided comprising a pharmaceutically acceptable carrier and one or more compounds of formula I or formula V above, or a pharmaceutically acceptable salt thereof.

According to another embodiment of the invention, a method of treating an individual for a proliferative disorder, particularly cancer, is provided, comprising administering to said individual an effective amount of a compound according to formulae I or V, or a pharmaceutically acceptable salt thereof, alone or in combination with a pharmaceutically acceptable carrier.

In another embodiment of the invention, a method of inhibiting growth of tumor cells in an individual afflicted with cancer is provided comprising administering to said individual an effective amount of a compound according to formulae I or V, or a pharmaceutically acceptable salt thereof, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of a compound according to formulae I or V, or a pharmaceutically acceptable salt thereof, alone or in combination with a pharmaceutically acceptable carrier.

DETAILED DESCRIPTION OF THE INVENTION

According to the present invention, certain α,β-unsaturated sulfones selectively kill various tumor cell types without killing normal cells. The sulfones of the present invention are characterized by cis-trans isomerism resulting from the presence of a double bond. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127–138. Stearic relations around a double bond are designated as "Z" or "E". Both configurations are included in the scope of the present invention.

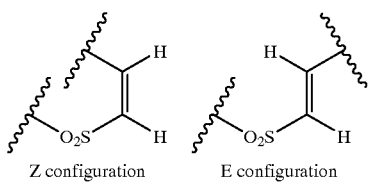

Z configuration    E configuration

According to one embodiment of the invention, the compound is according to formula I and has the E-configuration as shown in formula I. The compounds of formula I are characterized by the presence of two ring systems $Q_1$ and $Q_2$, at least one of which comprises a heterocyclic or multicyclic system. The other ring system, if not a heterocyclic or multicyclic system, comprises a substituted or unsubstituted phenyl radical according to formula II, above.

The ring systems $Q_1$ and $Q_2$ are optionally substituted. By "substituted" means that an atom or group of atoms has replaced hydrogen as the substituent attached to a ring carbon atom.

Any degree of substitution is possible on the phenyl ring of formula II. The substituents to replace hydrogen in the phenyl ring of formula II are selected from the group consisting of halogen, C1–C6 alkyl, C1–C6 alkoxy, nitro, cyano, carboxyl, hydroxyl, amino, C1–C6 trifluoroalkoxy and trifluoroalkoxy. By "halogen" is meant fluorine, chlorine, bromine or iodine. According to preferred embodiments, the substituents on the phenyl ring of formula II are selected from the group consisting of hydrogen, halogen, C1–C6 alkyl, C1–C6 alkoxy and trifluoromethyl.

Where a substituent is or contains an alkyl or alkoxy group, the carbon chain may be branched or straight, with straight being preferred. Preferably, the alkyl and alkoxy groups comprise C1–C3 alkyl and C1–C3 alkoxy, most preferably methyl and methoxy. The same preference holds true for the carbon chain in C1–C6 trifluoroalkoxy groups.

The phenyl ring may be up to penta-substituted, as shown in formula II. The pattern of multiple substitution with respect to the position of the phenyl ring of formula II may comprise any pattern of substitution. For example, tri-substitution may comprise substitution at positions 2, 3 and 4, positions 2, 4 and 5, or positions 2, 4 and 6, for example. Likewise, the pattern of tetra-substitution may comprise, for example, substitution at positions 2, 3, 4 and 5, or positions 2, 3, 5 and 6.

According to certain embodiments, the phenyl ring of formula II is tri-substituted, that is, only two of $R_1$ through $R_5$ are hydrogen. Representative combinations of substituents are set forth in Table 1:

TABLE 1

Tri-Substitution

| a | halogen | halogen | halogen |
|---|---|---|---|
| b | halogen | halogen | C1–C6 alkyl |
| c | halogen | halogen | C1–C6 alkoxy |
| d | halogen | halogen | nitro |
| e | halogen | halogen | carboxyl |
| f | halogen | C1–C6 alkyl | C1–C6 alkyl |
| g | halogen | C1–C6 alkoxy | C1–C6 alkoxy |
| h | C1–C6 alkyl | C1–C6 alkyl | C1–C6 alkyl |
| i | C1–C6 alkoxy | C1–C6 alkoxy | C1–C6 alkoxy |
| j | C1–C6 alkyl | C1–C6 alkyl | nitro |
| k | C1–C6 alkoxy | C1–C6 alkoxy | nitro |

According to certain other embodiments, the phenyl ring of formula II is tetra-substituted, that is, only one of $R_1$ through $R_5$ is hydrogen. Representative combinations of substituents are set forth in Table 2:

TABLE 2

Tetra-Substitution

| a | halogen | halogen | halogen | halogen |
|---|---|---|---|---|
| b | halogen | halogen | halogen | C1–C6 alkyl |
| c | halogen | halogen | halogen | C1–C6 alkoxy |
| d | halogen | halogen | halogen | nitro |
| e | halogen | halogen | C1–C6 alkyl | C1–C6 alkyl |
| f | halogen | halogen | C1–C6 alkoxy | C1–C6 alkoxy |
| g | C1–C6 alkyl | C1–C6 alkyl | C1–C6 alkyl | nitro |
| h | C1–C6 alkoxy | C1–C6 alkoxy | C1–C6 alkoxy | nitro |

According to other embodiments, the phenyl ring of formula II is penta-substituted, preferably with halogen, most preferably with the same halogen.

Where the phenyl ring is mono-substituted (only one of $R_1$–$R_5$ is other than hydrogen), the non-hydrogen substituent is preferably located at the 2- or 4-position ($R_1$ or $R_3$ is other than hydrogen). Where the ring is di-substituted (two of $R_1$–$R_5$ are other than hydrogen), the non-hydrogen substituents are preferably located at the 2- and 4-positions ($R_1$ and $R_3$ are other than hydrogen), or the 3- and 4-positions ($R_2$ and $R_3$ are other than hydrogen).

According to certain preferred embodiments, the 4-position of the phenyl ring of formula II is substituted, that is, $R_3$ is other than hydrogen. Preferably, $R_3$ is halogen or C1–C6 alkoxy in these embodiments. According to one preferred embodiment, $R_1$ is hydrogen or halogen; $R_3$ is halogen, C1–C3 alkoxy or trifluoromethyl; and $R_2$, $R_4$ and $R_5$ are hydrogen.

Where $Q_1$ of formula I is the 5- or 6-member aromatic heterocyclic radical of formula III, preferred radicals include 2-furyl, 3-furyl, 2-thienyl, 3-thienyl, 2-thienyl-1,1-dioxide, 3-thienyl-1,1-dioxide, 2-pyridyl and 3-pyridyl. The aforesaid heterocyclic radicals may be optionally mono- or di-substituted with halogen or nitro. Where $Q_2$ of formula I is the 5- or 6-member aromatic heterocyclic radical of formula IV, preferred radicals include 2-furyl, 3-furyl, 2-thienyl, 3-thienyl, 2-thienyl-1,1-dioxide, 3-thienyl-1,1-dioxide, 2-thiazolyl, 2-pyrrolyl, 2-pyridyl, 3-pyridyl and 4-pyridyl. The aforesaid heterocyclic radicals may be optionally mono- or di-substituted with halogen or nitro.

According to another embodiment of the invention, the α,β-unsaturated sulfone compound is of the Z-configuration and has the structure of formula V. The heterocyclic ring in formula V may be optionally mono- or di-substituted with halogen or nitro. Preferred heterocyclic radicals include unsubstituted 2-furyl, 3-furyl, 2-thienyl and 3-thienyl. The preferences for the substituent selection and pattern of substitution on the phenyl ring in formula V is the same as for formula II, above.

Without wishing to be bound by any theory, it is believed that the compounds of the invention affect the MAPK signal transduction pathway, thereby affecting tumor cell growth and viability. This cell growth inhibition is associated with regulation of the ERK and JNK types of MAPK. Without wishing to be bound by any theory, the sulfones of the present invention may block the phosphorylating capacity of ERK-2.

The compounds of the invention have been shown to inhibit the proliferation of tumor cells by inducing cell death. The compounds are believed effective against a broad range of tumor types, including but not limited to the following: breast, prostate, ovarian, lung, colorectal, brain (i.e, glioma) and renal. The compounds are also believed effective against leukemic cells. The compounds do not kill normal cells in concentrations at which tumor cells are killed.

The compounds of the invention may be administered to individuals (mammals, including animals and humans) afflicted with cancer.

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

Treatment of this broad range of tumor cells with the α,β-unsaturated sulfone compounds of the invention leads to inhibition of cell proliferation and induction of apoptotic cell death.

Tumor cells treated with the compounds of the invention accumulate in the G2/M phase of the cell cycle. As the cells exit the G2/M phase, they appear to undergo apoptosis. Treatment of normal cells with the sulfone compounds does not result in apoptosis.

The (E)-α,β, unsaturated sulfones of formula I may be prepared by Knoevenagel condensation of $Q_2$-aldehydes with $Q_1$—$CH_2$-sulfonyl acetic acids, according to the Scheme 1 below, wherein $Q_1$ and $Q_2$ are defined as for formula I, above. The $Q_1$—$CH_2$-thioacetic acid B is formed by the reaction of sodium thioglycollate and a $Q_1$—$CH_2$—Cl compound A. The thioacetic acid compound B is then oxidized with 30% hydrogen peroxide to give a corresponding sulfonyl acetic acid compound C. Condensation of C with the aldehyde D via a Knoevenagel reaction in the presence of benzylamine and glacial acetic acid yields the desired (E)-α,β-unsaturated sulfone E.

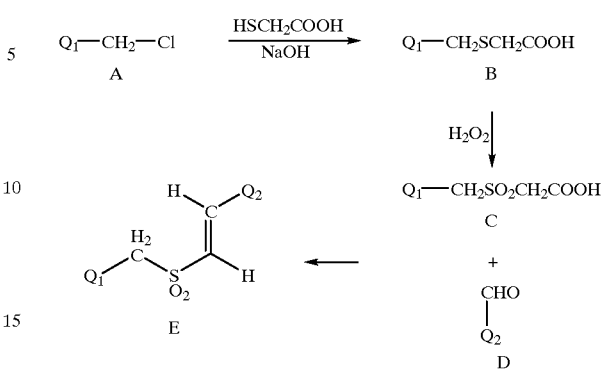

Scheme 1

The following is a more detailed two-part synthesis procedure for preparing the formula I α,β-unsaturated sulfones, (E)-$Q_1$—$CH_2SO_2CH$=$CH$—$Q_2$, according to the above scheme.

General Procedure 1: Synthesis (E)-α,β Unsaturated Sulfones

Part A. To a solution of (8 g, 0.2 mol) sodium hydroxide in methanol (200 ml), thioglycollic acid (0.1 mol) is added slowly and the precipitate formed is dissolved by stirring the contents of the flask. Then a compound $Q_1$—$CH_2$—Cl (0.1 mol) is added stepwise and the reaction mixture is refluxed for 2–3 hours. The cooled contents are poured onto crushed ice and neutralized with dilute hydrochloric acid (200 ml). The resulting corresponding thioacetic acid compound $Q_1$—$CH_2SCH_2COOH$ (0.1 mol) is subjected to oxidation with 30% hydrogen peroxide (0.12 mol) in glacial acetic acid (125 ml) by refluxing for 1 hour. The contents are cooled and poured onto crushed ice. The separated solid is recrystalized from hot water to give the corresponding pure sulfonylacetic acid $Q_1$—$CH_2SO_2CH_2COOH$.

Part B. A mixture of the sulfonyl acetic acid compound (10 mmol), an aldehyde $Q_2$—CHO (10 mmol), and benzylamine (200 ml) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields the desired α,β-unsaturated sulfone (E)-$Q_1$—$CH_2SO_2CH$=$CH$—$Q_2$ as a solid material.

According to an alternative to Part A, the appropriate sulfonylacetic acids may be generated by substituting a thioglycollate $HSCH_2COOR$ for thioglycollic acid, where R is an alkyl group, typically C1–C6 alkyl. This leads to the formation of the alkylthioacetate intermediate (F), $Q_1$—$CH_2SCH_2COOR$
F which is then converted to the corresponding thioacetic acid B by alkaline or acid hydrolysis.

The (Z)-α,β-unsaturated sulfones are prepared by the nucleophilic addition of the appropriate thiols to optionally substituted phenylacetylene with subsequent oxidation of the resulting sulfide by hydrogen peroxide. The procedure is analogous to the procedure generally described by Reddy et al., *Sulfur Letters* 13:83–90(1991)for the production of (Z)-styryl benzylsulfones, the entire disclosure of which is incorporated herein by reference.

In the first step of the (Z)-α,β-unsaturated sulfone synthesis, the sodium salt of an optionally mono- or di-substituted heterocyclic mercaptan of formula VI

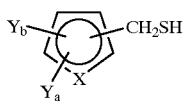
VI is allowed to react with phenylacetylene or the appropriate substituted phenylacetylene forming the pure Z-isomer of the corresponding (Z)-α,β-unsaturated sulfide in good yield.

In the second step of the synthesis, the (Z)-α,β-unsaturated sulfide intermediate is oxidized to the corresponding sulfone in the pure Z-isomeric form by treatment with hydrogen peroxide.

The following is a more detailed two-part synthesis procedure for preparing (Z)-α,β-unsaturated sulfones:

General Procedure 2: Synthesis of (Z)-α,β-unsaturated sulfones

Part A. To a refluxing methanolic solution of the sodium salt of a compound of formula VI, prepared from 460 mg (0.02 g atom) of (i) sodium, (ii) optionally mono- or di-substituted heterocyclic mercaptan of formula VI (0.02 mol) and (iii) 80 ml of absolute methanol, is added freshly distilled substituted or unsubstituted phenylacetylene. The mixture is refluxed for 20 hours, cooled and then poured on crushed ice. The crude product is filtered, dried and recrystalized from methanol or aqueous methanol to yield a pure (Z)-α,β-unsaturated sulfide.

Part B. An ice cold solution of the (Z)-α,β-unsaturated sulfide (3.0g) in 30 ml of glacial acetic acid is treated with 7.5 ml of 30% hydrogen peroxide. The reaction mixture is refluxed for 1 hour and then poured on crushed ice. The separated solid is filtered, dried, and recrystalized from 2-propanol to yield the pure (Z)-α,β-unsaturated sulfone. The purity of the compounds is ascertained by thin layer chromatography and the geometrical configuration is assigned by analysis of infrared and nuclear magnetic resonance spectral data.

The sulfone compounds of the present invention may be derivatized with a chemical group to permit conjugation to a carrier molecule, for the purpose of raising antibodies to the sulfones. Suitable derivatizing chemistries are well-known to those skilled in the art. Preferably, the derivative comprises a carboxylic acid derivative. The carrier may comprise any molecule sufficiently large to be capable of generating an immune response in an appropriate host animal. One such preferred carrier is keyhole limpet haemocyanin (KLH).

The present invention is also directed to isolated optical isomers of compounds according to formulae I and V. Certain compounds may have one or more chiral centers. By "isolated" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof. Isolated optical isomers may be purified from racemic mixtures by well-known chiral separation techniques. According to one such method, a racemic mixture of a compound having the structure of formula I or formula V, or chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

The compounds of the present invention may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I or V by reacting, for example, the appropriate acid or base with the compound of formula I or V.

The sulfones of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyper-proliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples. In each of the following examples, the sulfonyl acetic acid compound $Q_1CH_2SO_2CH_2COOH$ was made according to Part A of General Procedure 1: Synthesis (E)-$\alpha,\beta$ Unsaturated Sulfones, above. The final sulfone compound (E)-$Q_1$—$CH_2SO_2CH$=$CH$—$Q_2$ was recrystalized from 2-propanol and the purity was checked by thin layer chromatography. Compounds containing the 3-thienyl-1,1-dioxide group were generated by oxidizing the corresponding 3-thienyl sulfone.

EXAMPLE 1

(E)-2-pyridineethenyl-4-fluorobenzyl Sulfone

A solution of 4-fluorobenzylsulfonylacetic acid (10 mmol) and 2-pyridinecarboxaldehyde (10 mmol) was subjected to General Procedure 1, Part B. The title compound, melting point 110–111° C., was obtained in 54% yield.

EXAMPLE 2

(E)-3-pyridineethenyl-4-fluorobenzyl Sulfone

A solution of 4-fluorobenzylsulfonylacetic acid (10 mmol) and 3-pyridinecarboxaldehyde (10 mmol) was subjected to General Procedure 1, Part B. The title compound, melting point 155–156° C., was obtained in 60% yield.

EXAMPLE 3

(E)-4-pyridineethenyl-4-fluorobenzyl Sulfone

A solution of 4-fluorobenzylsulfonylacetic acid (10 mmol) and 4-pyridinecarboxaldehyde (10 mmol) was subjected to General Procedure 1, Part B. The title compound was obtained in 52% yield.

EXAMPLE 4

(E)-2-pyridineethenyl-4-chlorobenzyl Sulfone

A solution of 4-chlorobenzylsulfonylacetic acid (10 mmol) and 2-pyridinecarboxaldehyde (10 mmol) was subjected to General Procedure 1, Part B. The title compound, melting point 117–119° C., was obtained in 53% yield.

EXAMPLE 5

(E)-3-pyridineethenyl-4-chlorobenzyl Sulfone

A solution of 4-chlorobenzylsulfonylacetic acid (10 mmol) and 3-pyridinecarboxaldehyde (10 mmol) was subjected to General Procedure 1, Part B. The title compound, melting point 167–169° C., was obtained in 51 % yield.

EXAMPLE 6

(E)-4-pyridineethenyl-4-chlorobenzyl Sulfone

A solution of 4-chlorobenzylsulfonylacetic acid (10 mmol) and 4-pyridinecarboxaldehyde (10 mmol) was subjected to General Procedure 1, Part B. The title compound, melting point 107–109° C., was obtained in 53% yield.

EXAMPLE 7

(E)-2-pyridineethenyl-4-bromobenzyl Sulfone

A solution of 4-bromobenzylsulfonylacetic acid (10 mmol) and 2-pyridinecarboxaldehyde (10 mmol) was subjected to General Procedure 1, Part B. The title compound, melting point 143–145° C., was obtained in 52% yield.

EXAMPLE 8

(E)-3-pyridineethenyl-4-bromobenzyl Sulfone

A solution of 4-bromobenzylsulfonylacetic acid (10 mmol) and 3-pyridinecarboxaldehyde (10 mmol) was subjected to General Procedure 1, Part B. The title compound, melting point 161–162° C., was obtained in 59% yield.

EXAMPLE 9

(E)-4-pyridineethenyl-4-bromobenzyl Sulfone

A solution of 4-bromobenzylsulfonylacetic acid (10 mmol) and 4-pyridinecarboxaldehyde (10 mmol) was subjected to General Procedure 1, Part B. The title compound, melting point 158–160° C., was obtained in 54% yield.

EXAMPLE 10

(E)-2-thiopheneethenyl-4-fluorobenzyl Sulfone

A solution of 4-fluorobenzylsulfonylacetic acid (10 mmol) and 2-thiophenecarboxaldehyde (10 mmol) was subjected to General Procedure 1, Part B. The title compound, melting point 146–148° C., was obtained in 53% yield.

EXAMPLE 11

(E)-2-thiopheneethenyl-4-chlorobenzyl Sulfone

A solution of 4-chlorobenzylsulfonylacetic acid (10 mmol) and 2-thiophenecarboxaldehyde (10 mmol) was subjected to General Procedure 1, Part B. The title compound, melting point 158–159° C., was obtained in 56% yield.

EXAMPLE 12

(E)-2-thiopheneethenyl-4-bromobenzyl Sulfone

A solution of 4-bromobenzylsulfonylacetic acid (10 mmol) and 2-thiophenecarboxaldehyde (10 mmol) was subjected to General Procedure 1, Part B. The title compound, melting point 169–170° C., was obtained in 54% yield.

EXAMPLE 13

(E)-4-bromo-2-thiopheneethenyl-4-fluorobenzyl Sulfone

A solution of 4-fluorobenzylsulfonylacetic acid (10 mmol) and 4-bromo-2-thiophenecarboxaldehyde (10 mmol) was subjected to General Procedure 1, Part B. The title compound, melting point 155–157° C., was obtained in 54% yield.

EXAMPLE 14

(E)-4-bromo-2-thiopheneethenyl-4-chlorobenzyl Sulfone

A solution of 4-chlorobenzylsulfonylacetic acid (10 mmol) and 4-bromo-2-thiophenecarboxaldehyde (10 mmol) was subjected to General Procedure 1, Part B. The title compound, melting point 150–151° C., was obtained in 53% yield.

EXAMPLE 15

(E)4-bromo-2-thiopheneethenyl-4-bromobenzyl Sulfone

A solution of 4-bromobenzylsulfonylacetic acid (10 mmol) and 4-bromo-2-thiophenecarboxaldehyde (10 mmol) was subjected to General Procedure 1, Part B. The title compound, melting point 154–155° C., was obtained in 54% yield.

EXAMPLE 16

(E)-5-bromo-2-thiopheneethenyl-4-fluorobenzyl Sulfone

A solution of 4-fluorobenzylsulfonylacetic acid (10 mmol) and 5-bromo-2-thiophenecarboxaldehyde (10 mmol) was subjected to General Procedure 1, Part B. The title compound, melting point 161–162° C., was obtained in 55% yield.

EXAMPLE 17

(E)-5-bromo-2-thiopheneethenyl-4-chlorobenzyl Sulfone

A solution of 4-chlorobenzylsulfonylacetic acid (10 mmol) and 5-bromo-2-thiophenecarboxaldehyde (10 mmol) was subjected to General Procedure 1, Part B. The title compound, melting point 190–192° C., was obtained in 50% yield.

EXAMPLE 18

(E)-5-bromo-2-thiopheneethenyl-4-bromobenzyl Sulfone

A solution of 4-bromobenzylsulfonylacetic acid (10 mmol) and 5-bromo-2-thiophenecarboxaldehyde (10 mmol) was subjected to General Procedure 1, Part B. The title compound, melting point 199–202° C., was obtained in 52% yield.

EXAMPLE 19

(E)-2-thiophene-1,1-dioxoethenyl-4-fluorobenzyl Sulfone

A solution of the compound of Example 10 (500 mg) in glacial acetic acid (10 ml) and 30% hydrogen peroxide (1 ml) was refluxed for 1 hour and the cooled contents were poured onto crushed ice (100 g). The solid material separated was filtered and recrystallized from 2-propanol. The title compound, melting point 126–128° C., was obtained in 52% yield.

EXAMPLE 20

(E)-2-thiophene-1,1-dioxoethenyl-4-chlorobenzyl Sulfone

A solution of the compound of Example 11 (500 mg) in glacial acetic acid (10 ml) and 30% hydrogen peroxide (1 ml) was refluxed for 1 hour and the cooled contents were poured onto crushed ice (100 g). The solid material separated was filtered and recrystallized from 2-propanol. The title compound, melting point 108–110° C., was obtained in 55% yield.

EXAMPLE 21

(E)-2-thiophene-1,1-dioxoethenyl-4-bromobenzyl Sulfone

A solution of compound 12 (500 mg) in glacial acetic acid (10 ml) and 30% hydrogen peroxide (1 ml) was refluxed for 1 hour and the cooled contents were poured onto crushed ice (100 g). The solid material separated was filtered and recrystallized from 2-propanol. The title compound, melting point 145–147° C., was obtained in 56% yield.

EXAMPLE 22

(E)-3-thiopheneethenyl-4-fluorobenzyl Sulfone

A solution of 4-fluorobenzylsulfonylacetic acid (10 mmol) and 3-thiophenecarboxaldehyde (10 mmol) was subjected to General Procedure 1, Part B. The title compound, melting point 159–161° C., was obtained in 53% yield.

EXAMPLE 23

(E)-3-thiopheneethenyl-4-chlorobenzyl Sulfone

A solution of 4-chlorobenzylsulfonylacetic acid (10 mmol) and 3-thiophenecarboxaldehyde (10 mmol) was sub-

EXAMPLE 24

(E)-3-thiopheneethenyl-4-bromobenzyl Sulfone

A solution of 4-bromobenzylsulfonylacetic acid (10 mmol) and 3-thiophenecarboxaldehyde (10 mmol) was subjected to General Procedure 1, Part B. The title compound, melting point 175–177° C., was obtained in 70% yield.

EXAMPLE 25

(E)-3-thiopheneethenyl-4-iodobenzyl Sulfone

A solution of 4-iodobenzylsulfonylacetic acid (10 mmol) and 3-thiophenecarboxaldehyde (10 mmol) was subjected to General Procedure 1, Part B. The title compound, melting point 177–179° C., was obtained in 52% yield.

EXAMPLE 26

(E)-3-thiopheneethenyl-4-methylbenzyl Sulfone

A solution of 4-methylbenzylsulfonylacetic acid (10 mmol) and 3-thiophenecarboxaldehyde (10 mmol) was subjected to General Procedure 1, Part B. The title compound, melting point 135–136° C., was obtained in 55% yield.

EXAMPLE 27

(E)-3-thiopheneethenyl-4-methoxybenzyl Sulfone

A solution of 4-methoxybenzylsulfonylacetic acid (10 mmol) and 3-thiophenecarboxaldehyde (10 mmol) was subjected to General Procedure 1, Part B. The title compound, melting point 130–131° C., was obtained in 55% yield.

EXAMPLE 28

(E)-3-thiopheneethenyl-4-trifloromethoxylbenzyl Sulfone

A solution of 4-trifluoromethoxybenzylsulfonylacetic acid (10 mmol) and 3-thiophenecarboxaldehyde (10 mmol) was subjected to General Procedure 1, Part B. The title compound, melting point 201–202° C., was obtained in 52% yield.

EXAMPLE 29

(E)-3-thiopheneethenyl-2,4-dichlorobenzyl Sulfone

A solution of 2,4-dichlorobenzylsulfonylacetic acid (10 mmol) and 3-thiophenecarboxaldehyde (10 mmol) was subjected to General Procedure 1, Part B. The title compound, melting point 125–126° C., was obtained in 53% yield.

EXAMPLE 30

(E)-3-thiopheneethenyl-3,4-dichlorobenzyl Sulfone

A solution of 3,4-dichlorobenzylsulfonylacetic acid (10 mmol) and 3-thiophenecarboxaldehyde (10 mmol) was subjected to General Procedure 1, Part B. The title compound, melting point 152–153° C., was obtained in 51% yield.

EXAMPLE 31

(E)-3-thiopheneethenyl-4-cyanobenzyl Sulfone

A solution of 4-cyanobenzylsulfonylacetic acid (10 mmol) and 3-thiophenecarboxaldehyde (10 mmol) was subjected to General Procedure 1, Part B. The title compound, melting point 168–170° C., was obtained in 54% yield.

EXAMPLE 32

(E)-3-thiopheneethenyl-4-nitrobenzyl Sulfone

A solution of 4-nitrobenzylsulfonylacetic acid (10 mmol) and 3-thiophenecarboxaldehyde (10 mmol) was subjected to General Procedure 1, Part B. The title compound, melting point 203–205° C., was obtained in 54% yield.

EXAMPLE 33

(E)-3-thiophene-1,1-dioxoethenyl-4-fluorobenzyl Sulfone

A solution of the compound of Example 22 (500 mg) in glacial acetic acid (10 ml) and 30% hydrogen peroxide (1 ml) was refluxed for 1 hour and the cooled contents were poured onto crushed ice (100 g). The solid material separated was filtered and recrystallized from 2-propanol. The title compound, melting point 95–99° C., was obtained in 52% yield.

EXAMPLE 34

(E)-3-thiophene-1,1-dioxoethenyl-4-chlorobenzyl Sulfone

A solution of the compound of Example 23 (500 mg) in glacial acetic acid (10 ml) and 30% hydrogen peroxide (1 ml) was refluxed for 1 hour and the cooled contents were poured onto crushed ice (100 g. The solid material separated was filtered and recrystallized from 2-propanol. The title compound, melting point 115–120° C., was obtained in 51% yield.

EXAMPLE 35

(E)-3-thiophene-1,1-dioxoethenyl-4-bromobenzyl Sulfone

A solution of the compound of Example 24 (500 mg) in glacial acetic acid (10 ml) and 30% hydrogen peroxide (1 ml) was refluxed for 1 hour and the cooled contents were poured onto crushed ice (100 g. The solid material separated was filtered and recrystallized from 2-propanol. The title compound, melting point 152–155° C., was obtained in 50% yield.

EXAMPLE 36

(E)-3-thiophene-1,1-dioxoethenyl-4-methoxybenzyl Sulfone

A solution of the compound of Example 27 (500 mg) in glacial acetic acid (10 ml) and 30% hydrogen peroxide (1 ml) was refluxed for 1 hour and the cooled contents were poured onto crushed ice (100 g. The solid material separated was filtered and recrystallized from 2-propanol. The title compound, melting point 92–95° C., was obtained in 54% yield.

EXAMPLE 37

(E)-3-thiophene-1,1-dioxoethenyl-2,4-dichlorobenzyl Sulfone

A solution of the compound of Example 29 (500 mg) in glacial acetic acid (10 ml) and 30% hydrogen peroxide (1 ml) was refluxed for 1 hour and the cooled contents were poured onto crushed ice (100 g. The solid material separated was filtered and recrystallized from 2-propanol. The title compound, melting point 135–139° C., was obtained in 52% yield.

EXAMPLE 38

(E)-2-furanethenyl-4-fluorobenzyl Sulfone

A solution of 4-fluorobenzylsulfonylacetic acid (10 mmol) and 2-furancarboxaldehyde (10 mmol) was subjected to General Procedure 1, Part B. The title compound, melting point 103–105° C., was obtained in 53% yield.

EXAMPLE 39

(E)-2-furanethenyl-4-chlorobenzyl Sulfone

A solution of 4-chlorobenzylsulfonylacetic acid (10 mmol) and 2-furancarboxaldehyde (10 mmol) was subjected to General Procedure 1, Part B. The title compound, melting point 106–108° C., was obtained in 52% yield.

EXAMPLE 40

(E)-2-furanethenyl-4-bromobenzyl Sulfone

A solution of 4-bromobenzylsulfonylacetic acid (10 mmol) and 2-furancarboxaldehyde (10 mmol) was subjected to General Procedure 1, Part B. The title compound, melting point 125–127° C., was obtained in 52% yield.

EXAMPLE 41

(E)-3-furanethenyl-4-fluorobenzyl Sulfone

A solution of 4-fluorobenzylsulfonylacetic acid (10 mmol) and 3-furancarboxaldehyde (10 mmol) was subjected to General Procedure 1, Part B. The title compound, melting point 114–117° C., was obtained in 51% yield.

EXAMPLE 42

(E)-3-furanethenyl-4-chlorobenzyl Sulfone

A solution of 4-chlorobenzylsulfonylacetic acid (10 mmol) and 3-furancarboxaldehyde (10 mmol) was subjected to General Procedure 1, Part B. The title compound, melting point 154–156° C., was obtained in 50% yield.

EXAMPLE 43

(E)-3-furanethenyl-4-bromobenzyl Sulfone

A solution of 4-bromobenzylsulfonylacetic acid (10 mmol) and 3-furancarboxaldehyde (10 mmol) was subjected to General Procedure 1, Part B. The title compound, melting point 156–158° C., was obtained in 51% yield.

EXAMPLE 44

(E)-3-furanethenyl-4-iodobenzyl Sulfone

A solution of 4-iodobenzylsulfonylacetic acid (10 mmol) and 3-furancarboxaldehyde (10 mmol) was subjected to General Procedure 1, Part B. The title compound, melting point 166–170° C., was obtained in 52% yield.

EXAMPLE 45

(E)-3-furanethenyl-4-methylbenzyl Sulfone

A solution of 4-methylbenzylsulfonylacetic acid (10 mmol) and 3-furancarboxaldehyde (10 mmol) was subjected to General Procedure 1, Part B. The title compound, melting point 123–126° C., was obtained in 53% yield.

EXAMPLE 46

(E)-3-furanethenyl-4-methoxybenzyl Sulfone

A solution of 4-methoxybenzylsulfonylacetic acid (10 mmol) and 3-furancarboxaldehyde (10 mmol) was subjected to General Procedure 1, Part B. The title compound, melting point 117–119° C., was obtained in 51% yield.

EXAMPLE 47

(E)-3-furanethenyl-4-trifluoromethylbenzyl Sulfone

A solution of 4-trifluoromethylbenzylsulfonylacetic acid (10 mmol) and 3-furancarboxaldehyde (10 mmol) was subjected to General Procedure 1, Part B. The title compound, melting point 167–169° C., was obtained in 51% yield.

EXAMPLE 48

(E)-3-furanethenyl-2,4-dichlorobenzyl Sulfone

A solution of 2,4-dichlorobenzylsulfonylacetic acid (10 mmol) and 3-furancarboxaldehyde (10 mmol) was subjected to General Procedure 1, Part B. The title compound, melting point 104–106° C., was obtained in 53% yield.

EXAMPLE 49

(E)-3-furanethenyl-3,4-dichlorobenzyl Sulfone

A solution of 3,4-dichlorobenzylsulfonylacetic acid (10 mmol) and 3-furancarboxaldehyde (10 mmol) was subjected to General Procedure 1, Part B. The title compound, melting point 131–133° C., was obtained in 52% yield.

EXAMPLE 50

(E)-3-furanethenyl-4-cyanobenzyl Sulfone

A solution of 4-cyanobenzylsulfonylacetic acid (10 mmol) and 3-furancarboxaldehyde (10 mmol) was subjected to General Procedure 1, Part B. The title compound, melting point 175–178° C., was obtained in 53% yield.

EXAMPLE 51

(E)-3-furanethenyl-4-nitrobenzyl Sulfone

A solution of 4-nitrobenzylsulfonylacetic acid (10 mmol) and 3-furancarboxaldehyde (10 mmol) was subjected to General Procedure 1, Part B. The title compound, melting point 210–213° C., was obtained in 52% yield.

EXAMPLE 52

(E)-2-thiazoleethenyl-4-chlorobenzyl Sulfone

A solution of 4-chlorobenzylsulfonylacetic acid (10 mmol) and 2-thiazolecarboxaldehyde (10 mmol) was subjected to General Procedure 1, Part B. The title compound, melting point 133–137° C., was obtained in 51% yield.

EXAMPLE 53

(E)-2-pyrrolethenyl-4-chlorobenzyl Sulfone

A solution of 4-chlorobenzylsulfonylacetic acid (10 mmol) and 2-pyrrolecarboxaldehyde (10 mmol) was subjected to General Procedure 1, Part B. The title compound was obtained.

EXAMPLE 54

(E)-2-pyrrolethenyl-4-bromobenzyl Sulfone

A solution of 4-bromobenzylsulfonylacetic acid (10 mmol) and 2-pyrrolecarboxaldehyde (10 mmol) was subjected to General Procedure 1, Part B. The title compound was obtained.

EXAMPLE 55

(E)-2-nitro-4-thiopheneethenyl-4-chlorobenzyl Sulfone

A solution of 4-chlorobenzylsulfonylacetic acid (10 mmol) and 2-nitro-4-thiophenecarboxaldehyde (10 mmol) was subjected to General Procedure 1, Part B. The title compound, melting point 228–230° C., was obtained in 56% yield.

EXAMPLE 56

(E)-2-nitro-4-thiopheneethenyl-4-iodobenzyl Sulfone

A solution of 4-iodobenzylsulfonylacetic acid (10 mmol) and 2-nitro-4-thiophenecarboxaldehyde (10 mmol) was subjected to General Procedure 1, Part B. The title compound, melting point 177–179° C., was obtained in 67% yield.

EXAMPLE 57

(E)-2-nitro-4-thiopheneethenyl-2,4-dichlorobenzyl Sulfone

A solution of 2,4-dichlorobenzylsulfonylacetic acid (10 mmol) and 2-nitro-4-thiophenecarboxaldehyde (10 mmol) was subjected to General Procedure 1, Part B. The title compound, melting point 228–230° C., was obtained in 64% yield.

EXAMPLE 58

(E)-2-nitro-4-thiopheneethenyl-4-methoxybenzyl Sulfone

A solution of 4-methoxybenzylsulfonylacetic acid (10 mmol) and 2-nitro-4-thiophenecarboxaldehyde (10 mmol) was subjected to General Procedure 1, Part B. The title compound, melting point 170–172° C., was obtained in 56% yield.

EXAMPLE 59

(E)-1-piperazineethenyl-4-fluorobenzyl Sulfone

A solution of 4-fluorobenzylsulfonylacetic acid (10 mmol) and 1-piperazinecarboxaldehyde (10 mmol) was subjected to General Procedure 1, Part B. The title compound, melting point 156–157° C., was obtained in 50% yield.

EXAMPLE 60

(E)-1-piperazineethenyl-4-chlorobenzyl Sulfone

A solution of 4-chlorobenzylsulfonylacetic acid (10 mmol) and 1-piperazinecarboxaldehyde (10 mmol) was subjected to General Procedure 1, Part B. The title compound, melting point 126–128° C., was obtained in 50% yield.

EXAMPLE 61

(E)-1-piperazineethenyl-4-bromobenzyl Sulfone

A solution of 4-bromobenzylsulfonylacetic acid (10 mmol) and 1-piperazinecarboxaldehyde (10 mmol) was subjected to General Procedure 1, Part B. The title compound, melting point 128–129° C., was obtained in 52% yield.

EXAMPLE 62

(E)-1-naphthaleneethenyl-4-fluorobenzylsulfone

A solution of 4-fluorobenzylsulfonylacetic acid (10 mmol) and 1-naphthaldehyde (10 mmol) was subjected to General Procedure 1, Part B. The title compound, melting point 148–150° C., was obtained in 55% yield.

EXAMPLE 63

(E)-2-naphthaleneethenyl-4-fluorobenzylsulfone

A solution of 4-fluorobenzylsulfonylacetic acid (10 mmol) and 2-naphthaldehyde (10 mmol) was subjected to General Procedure 1, Part B. The title compound, melting point 185–186° C., was obtained in 58% yield.

EXAMPLE 64

(E)-1-naphthaleneethenyl-4-chlorobenzylsulfone

A solution of 4-chlorobenzylsulfonylacetic acid (10 mmol) and 1-naphthaldehyde (10 mmol) was subjected to General Procedure 1, Part B. The title compound, melting point 142–143° C., was obtained in 63% yield.

EXAMPLE 65

(E)-2-naphthaleneethenyl-4-chlorobenzylsulfone

A solution of 4-chlorobenzylsulfonylacetic acid (10 mmol) and 2-naphthaldehyde (10 mmol) was subjected to General Procedure 1, Part B. The title compound, melting point 191–193° C., was obtained in 52% yield.

EXAMPLE 66

(E)-1-naphthaleneethenyl-4-bromobenzylsulfone

A solution of 4-bromobenzylsulfonylacetic acid (10 mmol) and 1-naphthaldehyde (10 mmol) was subjected to General Procedure 1, Part B. The title compound, melting point 147–149° C., was obtained in 52% yield.

EXAMPLE 67

(E)-2-naphthaleneethenyl-4-bromobenzylsulfone

A solution of 4-bromobenzylsulfonylacetic acid (10 mmol) and 2-naphthaldehyde (10 mmol) was subjected to General Procedure 1, Part B. The title compound, melting point 193–194° C., was obtained in 54% yield.

EXAMPLE 68

(E)-4-fluorostyryl-1-(naphthylmethyl)sulfone

A solution of 1-(naphthylmethyl)sulfonylacetic acid (10 mmol) and 4-fluorobenzaldehyde (10 mmol) was subjected to General Procedure 1, Part B. The title compound, melting point 142–144° C., was obtained in 52% yield.

EXAMPLE 69

(E)-4-chlorostyryl-1-(naphthylmethyl)sulfone

A solution of 1-(naphthylmethyl)sulfonylacetic acid (10 mmol) and 4-chlorobenzaldehyde (10 mmol) was subjected

EXAMPLE 70

(E)-4-bromostyryl-1-(naphthylmethyl)sulfone

A solution of 1-(naphthylmethyl)sulfonylacetic acid (10 mmol) and 4-bromobenzaldehyde (10 mmol) was subjected to General Procedure 1, Part B. The title compound, melting point 207–209° C., was obtained in 55% yield

EXAMPLE 71

(E)-2-nitrostyryl-1-(naphthylmethyl)sulfone

A solution of 1-(naphthylmethyl)sulfonylacetic acid (10 mmol) and 2-nitrobenzaldehyde (10 mmol) was subjected to General Procedure 1, Part B. The title compound, melting point 188–192° C., was obtained in 62% yield

EXAMPLE 72

(E)-3-nitrostyryl-1-(naphthylmethyl)sulfone

A solution of 1-(naphthylmethyl)sulfonylacetic acid (10 mmol) and 3-nitrobenzaldehyde (10 mmol) was subjected to General Procedure 1, Part B. The title compound, melting point 192–194° C., was obtained in 59% yield.

EXAMPLE 73

(E)-4-nitrostyryl-1-(naphthylmethyl)sulfone

A solution of 1-(naphthylmethyl)sulfonylacetic acid (10 mmol) and 4-nitrobenzaldehyde (10 mmol) was subjected to General Procedure 1, Part B. The title compound, melting point 252–254° C., was obtained in 61% yield.

EXAMPLE 74

(E)-9-anthraceneethenyl-4-fluorobenzylsulfone

A solution of 4-fluorobenzylsulfonylacetic acid (10 mmol) and 9-anthraldehyde (10 mmol) was subjected to General Procedure 1, Part B. The title compound, melting point 93–95° C., was obtained in 56% yield.

EXAMPLE 75

(E)-9-anthraceneethenyl-4-chlorobenzylsulfone

A solution of 4-chlorobenzylsulfonylacetic acid (10 mmol) and 9-anthraldehyde (10 mmol) was subjected to General Procedure 1, Part B. The title compound, melting point 122–124° C., was obtained in 53% yield.

EXAMPLE 76

(E)-9-anthraceneethenyl-4-bromobenzylsulfone

A solution of 4-bromobenzylsulfonylacetic acid (10 mmol) and 9-anthraldehyde (10 mmol) was subjected to General Procedure 1, Part B. The title compound, melting point 172–175° C., was obtained in 51% yield.

Effect of Sulfones on Tumor Cell Lines

A. Cells

The effect of the sulfones on normal fibroblasts and on tumor cells of prostate, colon, lung and breast origin was examined utilizing the following cell lines: prostate tumor cell line DU-145; colorectal carcinoma cell line DLD-1; non-small cell lung carcinoma cell line H157; and breast tumor cell line BT-20. BT-20 is an estrogen-unresponsive cell line. NIH/3T3 and HFL are normal murine and human fibroblasts, respectively. BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH3T3 and HFL cells were grown in DMEM containing 10% calf serum supplemented with penicillin and streptomycin. All cell cultures were maintained at 37° C. in a humidified atmosphere of 5% $CO_2$.

B. Treatment with Sulfones and Viability Assay

Cells were treated with test compound at 2.5 mM concentration and cell viability was determined after 96 hours by the Trypan blue exclusion method. The results are set forth in Table 1. Activity for each compound is reported as a range of cell induced death (% Death) with the lowest activity in the range of 5–10%.

Normal cells HFL and NIH 3T3 were treated with the same compounds in Table 1 under the same conditions of concentration and time. The normal cells displayed 5% growth inhibition but no appreciable cell death. The percent cell death is scored in Table 1 as follows:

TABLE 1

Effect of Sulfones on Tumor cells

I

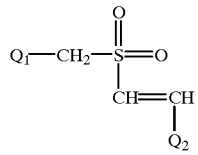

| | | | Tumor Cells | | | |
|---|---|---|---|---|---|---|
| Ex. | $Q_1$ | $Q_2$ | DU145 | DLD-1 | H157 | BT20 |
| 1 | 4-fluorophenyl | 2-pyridyl | + | + | + | + |
| 2 | 4-fluorophenyl | 3-pyridyl | + | + | + | + |
| 3 | 4-fluorophenyl | 4-pyridyl | ND | ND | ND | ND |
| 4 | 4-chlorophenyl | 2-pyridyl | + | + | + | + |
| 5 | 4-chlorophenyl | 3-pyridyl | + | + | + | + |
| 6 | 4-chlorophenyl | 4-pyridyl | + | + | + | + |
| 7 | 4-bromophenyl | 2-pyridyl | + | + | + | + |

TABLE 1-continued

Effect of Sulfones on Tumor cells

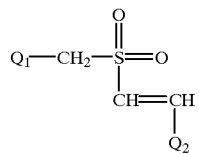

I

|     |                        |                          | Tumor Cells |       |       |       |
|-----|------------------------|--------------------------|-------|-------|-------|-------|
| Ex. | Q₁                     | Q₂                       | DU145 | DLD-1 | H157  | BT20  |
| 8   | 4-bromophenyl          | 3-pyridyl                | ++    | ++    | ++    | ++    |
| 9   | 4-bromophenyl          | 4-pyridyl                | +     | +     | +     | +     |
| 10  | 4-fluorophenyl         | 2-thienyl                | +     | +     | +     | +     |
| 11  | 4-chlorophenyl         | 2-thienyl                | +     | +     | +     | +     |
| 12  | 4-bromophenyl          | 2-thienyl                | +     | +     | +     | +     |
| 13  | 4-fluorophenyl         | 4-bromo-2-thienyl        | +     | +     | +     | +     |
| 14  | 4-chlorophenyl         | 4-bromo-2-thienyl        | +     | +     | +     | +     |
| 15  | 4-bromophenyl          | 4-bromo-2-thienyl        | +     | +     | +     | +     |
| 16  | 4-fluorophenyl         | 5-bromo-2-thienyl        | +     | +     | +     | +     |
| 17  | 4-chlorophenyl         | 5-bromo-2-thienyl        | +     | +     | +     | +     |
| 18  | 4-bromophenyl          | 5-bromo-2-thienyl        | +     | +     | +     | +     |
| 19  | 4-fluorophenyl         | 2-thienyl-1,1-dioxide    | ND    | ND    | ND    | ND    |
| 20  | 4-chlorophenyl         | 2-thienyl-1,1-dioxide    | ND    | ND    | ND    | ND    |
| 21  | 4-bromophenyl          | 2-thienyl-1,1-dioxide    | ND    | ND    | ND    | ND    |
| 22  | 4-fluorophenyl         | 3-thienyl                | +     | +     | +     | +     |
| 23  | 4-chlorophenyl         | 3-thienyl                | +++   | +++   | +++   | +++   |
| 24  | 4-bromophenyl          | 3-thienyl                | +++   | +++   | +++   | +++   |
| 25  | 4-iodophenyl           | 3-thienyl                | ++    | ++    | ++    | ++    |
| 26  | 4-methylphenyl         | 3-thienyl                | +     | +     | +     | +     |
| 27  | 4-methoxyphenyl        | 3-thienyl                | ++++  | ++++  | ++++  | ++++  |
| 28  | 4-trifluoromethylphenyl | 3-thienyl               | +     | +     | +     | +     |
| 29  | 2,4-dichlorophenyl     | 3-thienyl                | ++++  | ++++  | ++++  | ++++  |
| 30  | 3,4-dichlorophenyl     | 3-thienyl                | +     | +     | +     | +     |
| 31  | 4-cyanophenyl          | 3-thienyl                | +     | +     | +     | +     |
| 32  | 4-nitrophenyl          | 3-thienyl                | +     | +     | +     | +     |
| 33  | 4-fluorophenyl         | 3-thienyl-1,1-dioxide    | +     | +     | +     | +     |
| 34  | 4-chlorophenyl         | 3-thienyl-1,1-dioxide    | +     | +     | +     | +     |
| 35  | 4-bromophenyl          | 3-thienyl-1,1-dioxide    | +     | +     | +     | +     |
| 36  | 4-methoxyphenyl        | 3-thienyl-1,1-dioxide    | +     | +     | +     | +     |
| 37  | 2,4-dichlorophenyl     | 3-thienyl-1,1-dioxide    | ++    | ++    | ++    | ++    |
| 38  | 4-fluorophenyl         | 2-furyl                  | ND    | ND    | ND    | ND    |
| 39  | 4-chlorophenyl         | 2-furyl                  | ND    | ND    | ND    | ND    |
| 40  | 4-bromophenyl          | 2-furyl                  | ND    | ND    | ND    | ND    |
| 41  | 4-fluorophenyl         | 3-furyl                  | +     | +     | +     | +     |
| 42  | 4-chlorophenyl         | 3-furyl                  | +++++ | +++++ | +++++ | +++++ |
| 43  | 4-bromophenyl          | 3-furyl                  | +++++ | +++++ | +++++ | +++++ |
| 44  | 4-iodophenyl           | 3-furyl                  | +++++ | +++++ | +++++ | +++++ |
| 45  | 4-methylphenyl         | 3-furyl                  | ND    | ND    | ND    | ND    |
| 46  | 4-methoxyphenyl        | 3-furyl                  | +++++ | +++++ | +++++ | +++++ |
| 47  | 4-trifluoromethylphenyl | 3-furyl                 | ++++  | ++++  | ++++  | ++++  |
| 48  | 2,4-dichlorophenyl     | 3-furyl                  | +++++ | +++++ | +++++ | +++++ |
| 49  | 3,4-dichlorophenyl     | 3-furyl                  | +++++ | ++++  | ++++  | ++++  |
| 50  | 4-cyanophenyl          | 3-furyl                  | +     | +     | +     | +     |
| 51  | 4-nitrophenyl          | 3-furyl                  | +     | +     | +     | +     |
| 52  | 4-chlorophenyl         | 2-thiazolyl              | ND    | ND    | ND    | ND    |
| 53  | 4-chlorophenyl         | 2-pyrrolyl               | ND    | ND    | ND    | ND    |
| 54  | 4-bromophenyl          | 2-pyrrolyl               | ND    | ND    | ND    | ND    |
| 55  | 4-chlorophenyl         | 2-nitro-4-thienyl        | ++    | ++++  | +     | +     |
| 56  | 4-iodophenyl           | 2-nitro-4-thienyl        | +     | +     | +     | +     |
| 57  | 2,4-dichlorophenyl     | 2-nitro-4-thienyl        | ++    | ++    | +     | +     |
| 58  | 4-methoxyphenyl        | 2-nitro-4-thienyl        | ++++  | +++++ | +++++ | +++   |
| 59  | 4-fluorophenyl         | 1-piperazinyl            | ND    | ND    | ND    | ND    |
| 60  | 4-chlorophenyl         | 1-piperazinyl            | ND    | ND    | ND    | ND    |

TABLE 1-continued

Effect of Sulfones on Tumor cells

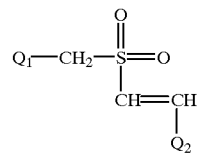

I

| | | | Tumor Cells | | | |
|---|---|---|---|---|---|---|
| Ex. | $Q_1$ | $Q_2$ | DU145 | DLD-1 | H157 | BT20 |
| 61 | 4-bromophenyl | 1-piperazinyl | ND | ND | ND | ND |
| 62 | 4-fluorophenyl | 1-naphthyl | + | + | + | + |
| 63 | 4-fluorophenyl | 2-naphthyl | + | + | + | + |
| 64 | 4-chlorophenyl | 1-naphthyl | ++ | ++ | ++ | ++ |
| 65 | 4-chlorophenyl | 2-naphthyl | + | + | + | + |
| 66 | 4-bromophenyl | 1-naphthyl | ++ | ++ | ++ | ++ |
| 67 | 4-bromophenyl | 2-naphthyl | + | + | + | + |
| 68 | 1-naphthyl | 4-fluorophenyl | + | + | + | + |
| 69 | 1-naphthyl | 4-chlorophenyl | + | + | + | + |
| 70 | 1-naphthyl | 4-bromophenyl | + | + | + | + |
| 71 | 1-naphthyl | 2-nitrophenyl | +++ | ND | ND | +++ |
| 72 | 1-naphthyl | 3-nitrophenyl | + | ND | ND | + |
| 73 | 1-naphthyl | 4-nitrophenyl | + | + | ++ | + |
| 74 | 4-fluorophenyl | 9-anthryl | +++ | ++++ | +++++ | ++++ |
| 75 | 4-chlorophenyl | 9-anthryl | ND | ND | ND | ND |
| 76 | 4-bromophenyl | 9-anthryl | ++++ | +++ | +++ | ++++ |

(−) = 0%
(+) = 5–10%
(++) = 10–15%
(+++) = 40–50%
(++++) = 50–60%
(+++++) = >80%
ND = not done.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. (amended) A compound of the formula I:

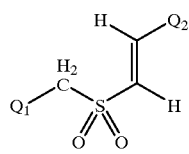

I wherein:

$Q_1$ is selected from the group consisting of
(a) a phenyl radical according to formula II

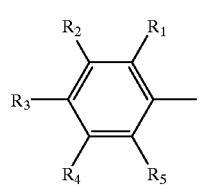

II wherein $R_1$, $R_2$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;

$R_3$ is selected from the group consisting of halogen, C1–C6 alkoxy, nitro, cyano, carboxyl, hydroxyl, amino, C1–C6 trifluoroalkoxy and trifluoromethyl;

(b) an aromatic radical selected from the group consisting of 1-naphthyl, 2-naphthyl and 9-anthryl; and (c) an aromatic radical according to formula III

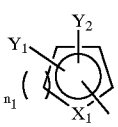

III wherein
$n_1$ is 1 or 2,
$Y_1$ and $Y_2$ are independently selected from the group consisting of hydrogen and halogen and
$X_1$ is selected from the group consisting of oxygen, nitrogen, sulfur and

;

$Q_2$ is selected from the group consisting of (d) a phenyl radical according to formula II

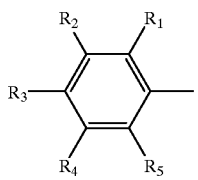

wherein
R$_1$, R$_2$, R$_1$ and R$_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
R$_3$ is selected from the group consisting of halogen, C1–C6 alkoxy, nitro, cyano, carboxyl, hydroxyl, amino, C1–C6 trifluoroalkoxy and trifluoromethyl;
(e) an aromatic radical selected from the group consisting of 1-naphthyl, 2- naphthyl and 9-anthryl;
(f) an aromatic radical according to formula IV

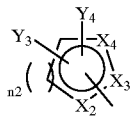

wherein
n$_2$ is 1 or 2,
Y$_3$ and Y$_4$ are independently selected from the group consisting of hydrogen, halogen, and nitro, and
X$_2$, X$_3$ and X$_4$ are independently selected from the group consisting of carbon, oxygen, nitrogen, sulfur and

provided that not all of X$_2$, X$_3$ and X$_4$ may be carbon; and
(g) 1-piperazinyl;
provided that at least one of Q$_1$ or Q$_2$ is other than a phenyl radical according to formula II;
or a pharmaceutically acceptable salt thereof.

2. A compound according to claim 1 wherein Q$_1$ is a phenyl radical according to formula II

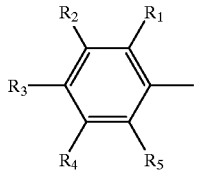

wherein
R$_1$, R$_2$, R$_4$ and R$_5$ are independently selected from the group consisting of hydrogen, halogen, C1–C6 alkyl. C1 –C6 alkoxy, nitro, cyano, carboxyl, hydroxyl, amino, C1 –C6 trifluoroalkoxy and trifluoromethyl;
R$_3$ is selected from the group consisting of halogen, C1–C6 alkoxy, nitro, cyano, carboxyl, hydroxyl, amino, C1–C6 trifluoroalkoxy and trifluoromethyl; or a pharmaceutically acceptable salt thereof.

3. A compound according to claim 2 wherein R$_1$, R$_2$, R$_4$ and R$_5$ are independently selected from the group consisting of hydrogen, halogen, C$_1$–C$_3$ alkoxy and trifluoromethyl, and R$_3$ is selected from the group consisting of halogen, C$_1$–C6 alkoxy and trifluoromethyl.

4. The compound according to claim 3 which is (E)-3-furanethenyl-3,4-dichlorobenzyl sulfone.

5. A compound according to claim 3 wherein R$_1$ is hydrogen or halogen; and R$_2$, R$_4$ and R$_5$ are hydrogen.

6. A compound according to claim 5 wherein Q$_2$ is selected from the group consisting of 3-furyl, 3-thienyl, 3-thienyl-1-dioxide, 2-nitro-4-thienyl, 9-anthryl, 1-naphthyl and 2-naphthyl.

7. The compound according to claim 5 which is (E)-3-thiopheneethenyl-4-chlorobenzyl sulfone.

8. The compound according to claim 5 which is (E)-3-thiopheneethenyl-4-bromobenzyl sulfone.

9. The compound according to claim 5 which is (E)-3-thiopheneethenyl-4-methoxybenzyl sulfone.

10. The compound according to claim 5 which is (E)-3-thiopheneethenyl-2,4-dichlorobenzyl sulfone.

11. The compound according to claim 5 which is (E)-3-thiophene-1,1-dioxoethenyl-2,4-dichlorobenzyl sulfone.

12. The compound according to claim 5 which is (E)-3-furanethenyl-4-chlorobenzyl sulfone.

13. The compound according to claim 5 which is (E)-3-furanethenyl-4-bromobenzyl sulfone.

14. The compound according to claim 5 which is (E)-3-furanethenyl-4-iodobenzyl sulfone.

15. The compound according to claim 5 which is (E)-3-furanethenyl-4-methoxybenzyl sulfone.

16. The compound according to claim 5 which is (E)-3-furanethenyl-4-trifluoromethylbenzyl sulfone.

17. The compound according to claim 5 which is (E)-3-furanethenyl-2,4-dichlorobenzyl sulfone.

18. The compound according to claim 5 which is (E)-2-nitro-4-thiopheneethenyl-4-chlorobenzyl sulfone.

19. The compound according to claim 5 which is (E)-2-nitro-4-thiopheneethenyl-4-methoxybenzyl sulfone.

20. The compound according to claim 5 which is (E)-9-anthraceneethenyl-4-fluorobenzylsulfone.

21. The compound according to claim 5 which is (E)-9-anthraceneethenyl-4-chlorobenzylsulfone.

22. The compound according to claim 5 which is (E)-9-anthraceneethenyl-4-bromobenzylsulfone.

23. A compound according to claim 1 wherein Q$_1$ is 1-naphthyl or 2-naphthyl and Q$_2$ is a phenyl radical according to formula II

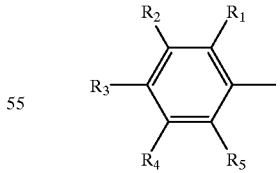

wherein:
R$_1$, R$_2$, R$_4$ and R$_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
R$_3$ is selected from the group consisting of halogen, C1–C6 alkoxy, nitro, cyano, carboxyl, hydroxyl, amino, C1–C6 trifluoroalkoxy and trifluoromethyl;

24. A compound selected from the group consisting of (E)-2-nitrostyryl-1- (naphthylmethyl)sulfone, (E)-3-nitrostyryl-1-(naphthylmethyl)sulfone and (E)-4-nitrostyryl-1- (naphthylmethyl)sulfone.

25. A compound of the formula V:

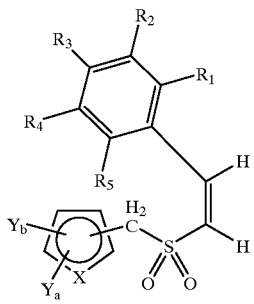

V wherein:

X is sulfur or oxygen; $Y_a$ and $Y_b$ are independently selected from the group consisting of hydrogen, halogen, and nitro; and $R_1$, $R_2$, $R_3$, $R_4$ and $R_5$ are independently selected from the group consisting of halogen, C1—C6 alkyl, C1—C6 alkoxy, nitro, cyano, carboxyl, hydroxyl, amino, C1—C6 trifluoroalkoxy and trifluoromethyl;

or a pharmaceutically acceptable salt thereof.

26. An isolated optical isomer of a compound according to claim 1, or pharmaceutically acceptable salt thereof.

27. An isolated optical isomer of a compound according to claim 25, or pharmaceutically acceptable salt thereof.

28. A pharmaceutical composition comprising a pharmaceutically acceptable carrier and a compound of the formula V:

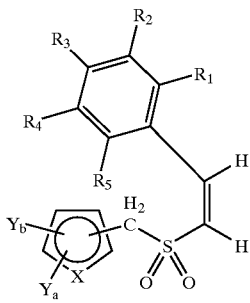

V wherein:

X is sulfur or oxygen; $Y_a$ and $Y_b$ are independently selected from the group consisting of hydrogen, halogen, and nitro; and $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, amino, C1–C6 trifluoroalkoxy and trifluoromethyl;

or a pharmaceutically acceptable salt thereof.

29. A pharmaceutical composition comprising a pharmaceutically acceptable carrier and a compound according to formula I:

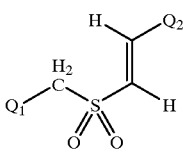

I wherein:

$Q_1$ is selected from the group consisting of
(a) a phenyl radical according to formula II

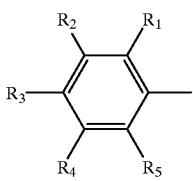

II wherein
$R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;

(b) an aromatic radical selected from the group consisting of 1-naphthyl, 2- naphthyl and 9-anthryl; and (c) an aromatic radical according to formula III

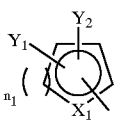

III wherein $n_1$ is 1 or 2, $Y_1$ and $Y_2$ are independently selected from the group consisting of hydrogen, halogen, and nitro, and $X_1$ is selected from the group consisting of oxygen, nitrogen, sulfur and

$Q_2$ is selected from the group consisting of
(d) a phenyl radical according to formula II

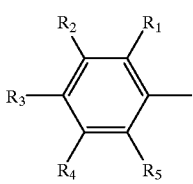

II wherein
$R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;

(e) an aromatic radical selected from the group consisting of 1-naphthyl, 2-naphthyl and 9-anthryl;

(f) an aromatic radical according to formula IV

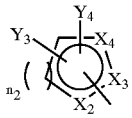

IV wherein
$n_2$ is 1 or 2,
$Y_3$ and $Y_4$ are independently selected from the group consisting of hydrogen, halogen, and nitro, and
$X_2$, $X_3$ and $X_4$ are independently selected from the group consisting of carbon, oxygen, nitrogen, sulfur and

provided that not all of $X_2$, $X_3$ and $X_4$ may be carbon; and (g) 1-piperazinyl;
provided that at least one of $Q_1$ or $Q_2$ is other than a phenyl radical according to formula II;
or a pharmaceutically acceptable salt thereof.

30. A method of treating an individual for a proliferative disorder comprising administering to said individual an effective amount of a pharmaceutical composition according to claim 29 or 28.

31. A method according to claim 30 wherein the proliferative disorder is selected from the group consisting of hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

32. A method according to claim 30 wherein the proliferative disorder is cancer.

33. A method according to claim 32 wherein the cancer is selected from the group consisting of ovarian, breast, prostate, lung, renal, colorectal and brain cancers, or the cancer is a leukemia.

34. A method of inducing apoptosis of tumor cells in an individual afflicted with cancer comprising administering to said individual an effective amount of a pharmaceutical composition according to claim 29 or 28.

35. A method according to claim 28 wherein the tumor cells are selected from the group consisting of ovarian, breast, prostate, lung, colorectal, renal and brain tumors.

36. A process for preparing a compound of claim 1 comprising condensing a compound of formula Ia

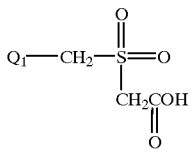

Ia with a compound of the formula

wherein:
$Q_1$ is selected from the group consisting of
(a) a phenyl radical according to formula II

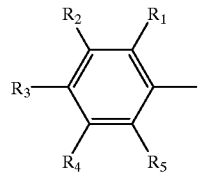

II wherein
$R_1$, $R_2$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
$R_3$ is selected from the group consisting of halogen, C1–C6 alkoxy, nitro, cyano, carboxyl, hydroxyl, amino, C1–C6 trifluoroalkoxy and trifluoromethyl;

(b) an aromatic radical selected from the group consisting of 1-naphthyl, 2-naphthyl and 9-anthryl; and
(c) an aromatic radical according to formula III

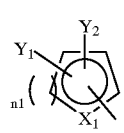

III wherein $n_1$ is 1 or 2, $Y_1$ and $Y_2$ are independently selected from the group consisting of hydrogen and halogen and $X_1$ is selected from the group consisting of oxygen, nitrogen, sulfur and

$Q_2$ is selected from the group consisting of
(d) a phenyl radical according to formula II

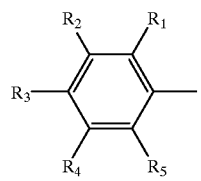

II wherein
$R_1$, $R_2$, $R_4$ and $R_5$ are independently selected from the group consisting of hydrogen, halogen, C1–C6 alkyl, C1–C6 alkoxy, nitro, cyano, carboxyl, hydroxyl, amino, C1–C6 trifluoroalkoxy and trifluoromethyl;
$R_3$ is selected from the group consisting of halogen, C1–C6 alkoxy, nitro, cyano, carboxyl, hydroxyl, amino, C1–C6 trifluoroalkoxy and trifluoromethyl;

(e) an aromatic radical selected from the group consisting of 1-naphthyl, 2- naphthyl and 9-anthryl;
(f) an aromatic radical according to formula IV

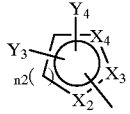   IV wherein
n$_2$ is 1 or 2,
Y$_3$ and Y$_4$ are independently selected from the group consisting of hydrogen, halogen, and nitro, and
X$_2$, X$_3$ and X$_4$ independently selected from the group consisting of carbon, oxygen, nitrogen, sulfur and

provided that not all of X$_2$, X$_3$ and X$_4$ maybe carbon; and
(g) 1-piperazinyl;
provided that at least one of Q$_1$ or Q$_2$ is other than a phenyl radical according to formula II.

37. A process according to claim 36 wherein the formula Ia compound is prepared by reacting sodium glycollate with a compound of the formula Q$_1$CH$_2$Cl to form a thioacetic compound of the formula

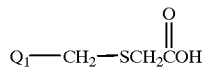

which is then oxidized to form a compound of formula Ia.

38. A process according to claim 36 wherein the thioacetic acid compound Q$_1$CH$_2$SCH$_2$COOH is prepared by reacting a compound of the formula HSCH$_2$COOR, where R is C1–C6 alkyl, with a compound of the formula Q$_1$CH$_2$Cl to form an intermediate of the formula:

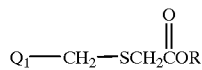

and hydrolyzing said intermediate to obtain said thioacetic acid compound Q$_1$CH$_2$SCH$_2$COOH.

39. A process for preparing a compound of claim 25 comprising reacting a compound of the formula

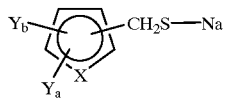

with a compound of the formula

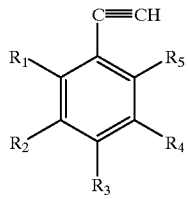

to form a sulfide compound of formula Va:

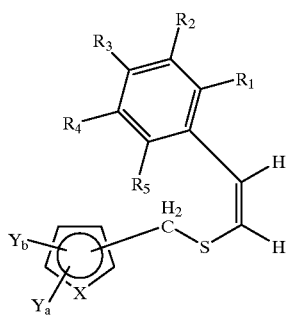

and oxidizing said formula Va compound to form a compound according to claim 25,
wherein:
X is sulfur or oxygen; Y$_a$ and Y$_b$ are independently selected from the group consisting of hydrogen, halogen, and nitro; and R$_1$, R$_2$, R$_3$, R$_4$ and R$_5$ are independently selected from the group consisting of halogen, C1–C6 alkyl, C1–C6 alkoxy, nitro, cyano, carboxyl, hydroxyl, amino, C1–C6 trifluoroalkoxy and trifluoromethyl.

40. A method according to claim 33 wherein the cancer is selected from the group consisting of breast, prostate, non-small cell lung and colorectal cancers.

41. A method according to claim 35 wherein the tumor cells are selected from the group consisting of breast, prostate, non-small cell lung and colorectal tumors.

* * * * *

UNITED STATES PATENT AND TRADEMARK OFFICE
CERTIFICATE OF CORRECTION

PATENT NO. : 6,541,475 B2
DATED : April 1, 2003
INVENTOR(S) : Reddy et al.

It is certified that error appears in the above-identified patent and that said Letters Patent is hereby corrected as shown below:

Column 5,
Line 43, delete the second occurrence of "of the".

Column 12,
Line 9, change "or" to -- of --.
Line 24, delete the second occurrence of "salicyclic,".
Line 29, delete "salicyclic,".

Column 13,
Line 7, insert -- be -- after "may".
Line 38, insert -- , -- after "agents".

Column 18,
Lines 32, 44 and 57, insert -- ) -- after "(100 g".

Column 19,
Line 2, insert -- ) -- after "(100 g".

Column 23,
Lines 2, 10 and 19, insert -- . -- after "yield".

Column 27,
Line 44, delete "(amended)".

Column 29,
Line 11, change the second occurrence of "$R_1$" with -- $R_4$ --.

Column 33,
Line 53, change "c1aim" to -- claim --.
Line 54, change "28" to -- 34 --.

UNITED STATES PATENT AND TRADEMARK OFFICE
CERTIFICATE OF CORRECTION

PATENT NO. : 6,541,475 B2
DATED : April 1, 2003
INVENTOR(S) : Reddy et al.

It is certified that error appears in the above-identified patent and that said Letters Patent is hereby corrected as shown below:

<u>Column 35,</u>
Line 24, change "maybe" to -- may be --.

Signed and Sealed this

Seventh Day of October, 2003

JAMES E. ROGAN
*Director of the United States Patent and Trademark Office*